United States Patent [19]

Walters et al.

[11] 4,049,003
[45] Sept. 20, 1977

[54] DIGITAL CARDIAC PACER

[75] Inventors: Robert A. Walters, Pittsburgh; Steve A. Kolenik, Leechburg, both of Pa.

[73] Assignee: ARCO Medical Products Company, Leechburg, Pa.

[21] Appl. No.: 654,504

[22] Filed: Feb. 2, 1976

Related U.S. Application Data

[63] Continuation-in-part of Ser. No. 625,295, Oct. 23, 1975, abandoned.

[51] Int. Cl.² .............................................. A61N 1/36
[52] U.S. Cl. .............................................. 128/419 PG
[58] Field of Search ........... 128/419 C, 419 E, 419 P, 128/419 PG, 419 R, 421, 422, 423

[56] References Cited

U.S. PATENT DOCUMENTS

| | | | |
|---|---|---|---|
| 3,557,796 | 1/1971 | Keller, Jr. et al. | 128/419 PG |
| 3,833,005 | 9/1974 | Wingrove | 128/419 PG |
| 3,920,024 | 11/1975 | Bowers | 128/419 PG |
| 3,921,642 | 11/1975 | Preston et al. | 128/419 PG |

*Primary Examiner*—William E. Kamm
*Attorney, Agent, or Firm*—Richard A. Bachand

[57] ABSTRACT

A digital cardiac pacer has an asynchronous interval counter to count clock pulses to establish a stimulation interval at the end of which it produces a pulse for initiating a stimulation pulse. A control counter to which amplified naturally occurring heat pulses or stimulation pulses are applied controls the delivery of a resetting pulse to the asynchronous interval counter to reinitiate its count. If the stimulation, heart, or an interference pulse is detected during the count of a "refractory period," the control counter is reset and the refractory period is extended. If another stimulation, heart, or interference, pulse is detected during the extended refractory period, no resetting pulse is delivered, and the asynchronous interval counter continues its normal count. If during the period of time following the extended refractory period a stimulation, heart, or interference pulse is received, the control counter produces a resetting pulse to reset the asynchronous interval counter. A delay circuit between the control and asynchronous counters causes the stimulation interval to be shortened during the reception of interference pulses.

6 Claims, 4 Drawing Figures

DIGITAL CARDIAC PACER

CROSS-REFERENCE TO RELATED APPLICATIONS

This application is a continuation-in-part of copending patent application Ser. No. 625,295 filed Oct. 23, 1975 now abandoned.

BACKGROUND OF THE INVENTION

1. Field of the Invention

This invention relates to cardiac pacers and more particularly to improvements in digital circuit means for generating cardiac stimulation pulses.

2. Description of the Prior Art

Berkovits U.S. Pat. No. 3,345,990 employs a pair of thyratrons for disabling the transmission of a generated pulse to the heart during intervals when the circuitry detects an R-wave produced by the heart. Previous demand circuitry had used other approaches for responding to the signals from normal heart operation.

Keller U.S. Pat. No. 3,557,796 describes a demand heart pacer comprising a clock, a counter generating pulses at a rate appropriate for cardiac stimulation signals, circuit means detecting signals from the heart, noise discrimination counters in such heart signal detection circuit means, and coupling means for disabling such cardiac stimulating signals when appropriate naturally occurring heart signals are detected.

Gobeli U.S. Pat. No. Re. 28,003 describes a pacer which, when subjected to electromagnetic interference, operates at a rate different than its normal demand rate.

Greatbatch U.S. Pat. No. 3,870,050 describes a demand cardiac pacer comprising a clock, a counter, and means inhibiting the transmission of signals from the counter whenever an appropriate signal is detected from normal operation of the heart.

Although digital pacers have been proposed, cardiologists have persisted in making more extensive use of other types of pacers.

SUMMARY OF THE INVENTION

In light of the above, it is, therefore, an object of the invention to provide a digital heart pacer.

It is another object of the invention to provide a digital heart pacer which provides a capability for asynchronous, demand, and interference mode operation.

It is another object of the invention to provide a heart pacer which has an interference mode operation and a demand mode operation with different interpulse periods.

It is still another object of the invention to provide a digital heart pacer which provides a variable control interval during which reception of an R-wave or R-wave simulating signal does not reset a stimulation pulse controlling asynchronous interval counter, and which provides a following alert interval during which such R-wave or R simulating signal resets the asynchronous interval counter, the control interval including an interval the count of which must be uninterruptedly reached immediately prior to the initiation of the alert interval period.

It is another object of the invention to provide a digital heart pacer which can be implanted within or used externally to a patient.

These and other object, features and advantages will become apparent to those skilled in the art from the following detailed description when read in conjunction with the accompanying drawings and appended claims.

In the realization of the aforementioned objects, the digital cardiac pacer, in accordance with the invention, includes an asynchronous interval counter for counting pulses from a source of clock pulses. Upon reaching a predetermined count, the asynchronous interval counter produces an output which is applied to an output pulse width regulator to insure a constant output pulse width. The constant width pulse is applied to a voltage multiplying amplifier for delivery to heart associated electrodes.

An R-wave amplifier is provided to detect R-wave signals and signals simulating R-wave signals, having an output connected to a resetting control of a control counter. The control counter also connected to receive clock pulses counts an interval after which reception of a resetting R-wave signal from the R-wave detector causes a change in state of the output. Prior to the reaching of the count, the reception of an R-wave signal from the R-wave detector merely resets the control counter without producing a change in the state of its output. The control counter, thereby, defines a control state, prior to its reaching its predetermined count, which can be indefinitely prolonged, and an alert state, after which reception of an R-wave produces a change in output state. The change in output state is applied to a delay circuit, which, after a predetermined time delay, produces a resetting signal to the asynchronous interval counter.

The circuit, thus configured, produces heart stimulation pulses at a first demand mode rate and at a second, shorter, asynchronous mode rate.

BRIEF DESCRIPTION OF THE DRAWING

The invention is illustrated in the accompanying drawing, wherein.

In the various figures of the drawing, like reference numerals are used to denote like parts.

DETAILED DESCRIPTION OF THE PREFERRED EMBODIMENTS

Figure 1:
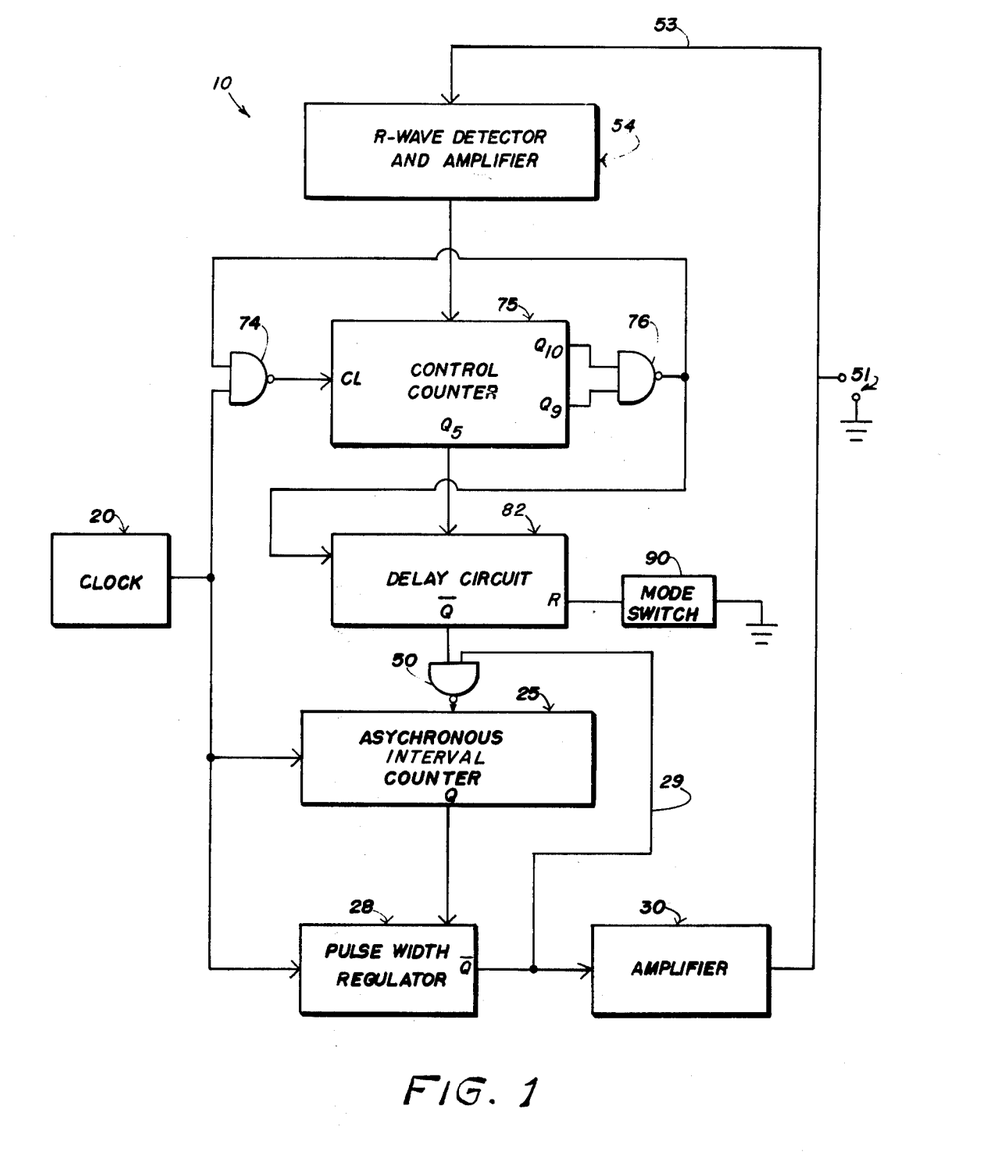
FIG. 1 is a box diagram of the digital cardiac pacer, in accordance with the principles of the invention.
Figure 2:
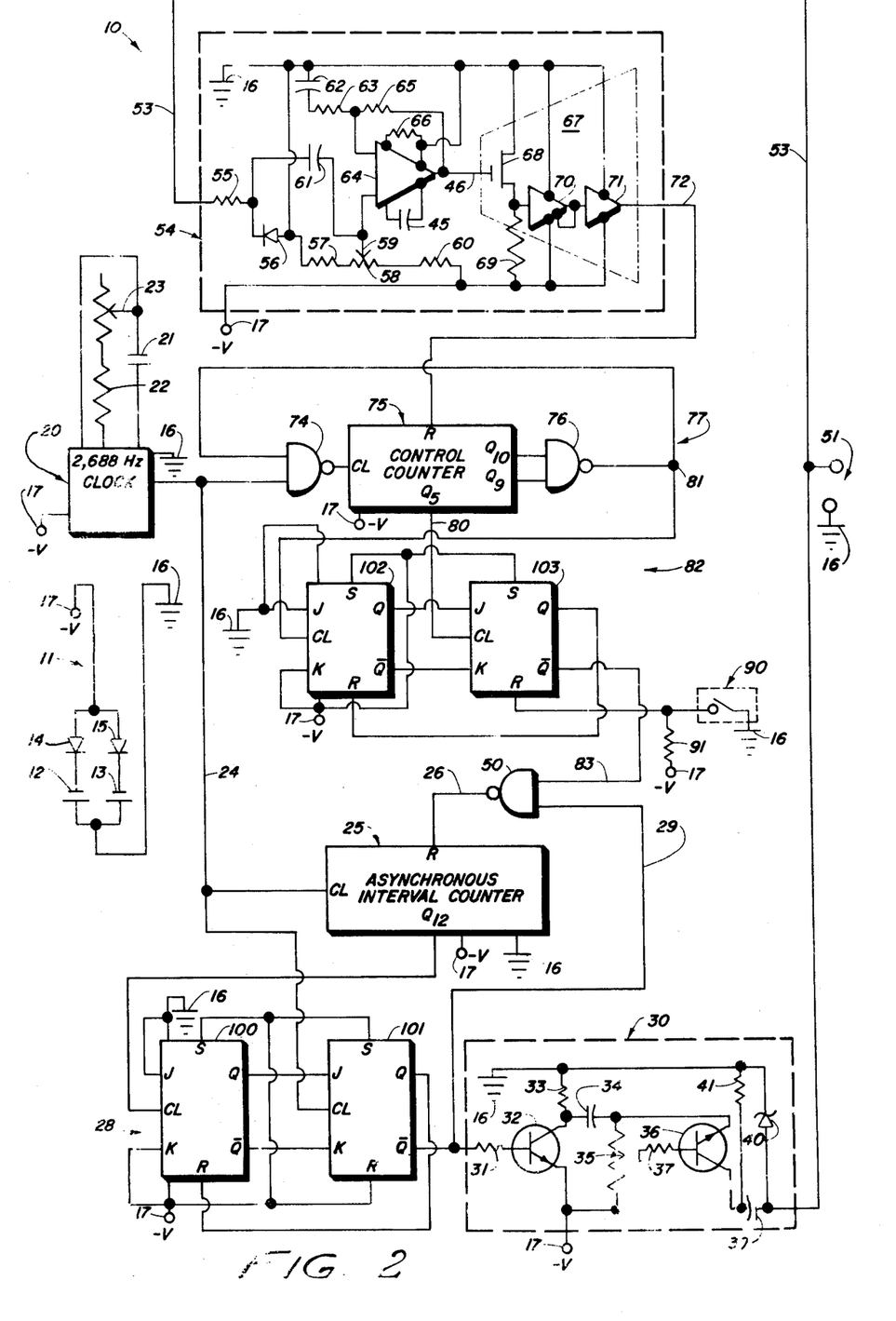
FIG. 2 is a more detailed box diagram of the digital cardiac pacer of FIG. 1.
Figure 4:
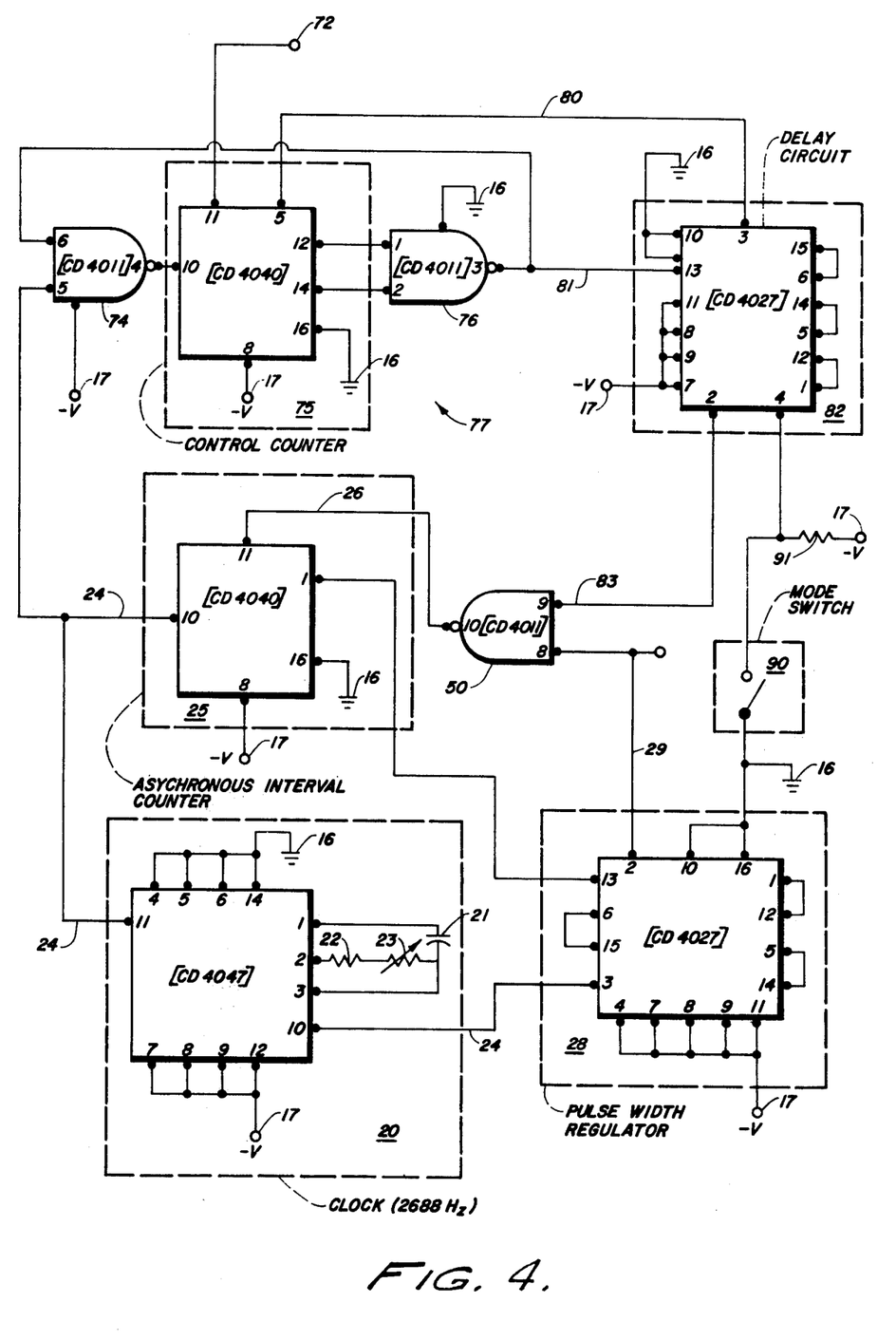
FIG. 4 is a box diagram of the circuit of FIG. 2 illustrating the various connections to specific integrated circuit packages, in an illustrative embodiment of the digital cardiac pacer of the invention.

A digital pacer 10, in accordance with the invention, is shown in box diagram form in FIGS. 1 and 2, and in a particular integrated circuit configuration in FIG. 4. The pacer embodiment illustrated detects naturally produced signals from and provides stimulation signals for application to a heart, the manner of such signal application and detection being well known in the art.

The present invention is applicable to external pacers and console systems, as well as to implantable pacers, so that the output terminal system 51 is intended broadly to be connectable to any system intended to associate the pacer with appropriate zones of the heart.

The pacer of the invention is adapted to detect naturally occurring heart pulses (referred to here generally as heart pulses, and specifically as particular pulses, such as R-waves, P-waves, etc.). It should be noted that although some pacers detect P-waves, or other heart generated signals, most demand pacers respond to R-waves; and the illustrative example features R-wave responsiveness, without losing perspective on the other heartbeat signal possibilities. The circuit is intended to provide a stimulation signal (referred to here as a stimulation pulse) under certain conditions, below described. Also, interference (referred to here as interference pulses) simulating an R-wave may be detected by the circuit in some instances, as below explained.

With reference now to FIG. 1, the pacer 10 includes a clock 20 which provides clock pulses of relatively high frequency, compared to a frequency of a normal heartbeat. For instance, the clock frequency can conveniently be of approximately 2,688 Hertz.

An asynchronous rate or interval counter 25 receives, pulses from the clock 20, counts a predetermined number of them, and, unless reset, produces an output upon reaching the predetermined count. Thus, absent other circuit operations, as below detailed, the asynchronous interval counter 25 produces a pulse for initiating a stimulation pulse at desired heartbeat intervals of, for example, about 800 milliseconds.

A pulse width regulator 28 receives pulses from the clock 20, and is triggered by the output from the asynchronous interval counter 25. The pulse width regulator 28 assures that the width of the pulse output is sufficient for delivery to an output amplifier 30 to produce a satisfactory stimulation pulse to the output line 53 for delivery to the output electrodes 51.

Additionally, a line 29 is gated from the output of the pulse width regulator to a resetting input of the asynchronous interval counter 25 to reinitiate its count upon delivery of a stimulation pulse therefrom.

The circuit thus described fulfills the function of a fixed rate pacer, continuously supplying stimulation pulses at the rate determined by the asynchronous interval counter 25 and the frequency of the clock 20. To effect the demand capability of the pacer, heart signal detecting circuitry is employed to reset the asynchronous interval counter upon the occurrence of a heart pulse from the heart with which the pacer is associated. The heart pulses are detected upon the electrodes 51, and conducted upon the line 53 to an R-wave detector and amplifier 54. The R-wave detector and amplifier 54 contains filters and amplifiers for emphasizing signals of the R-wave frequency to the exclusion of others.

The output of the R-wave detector and amplifier 54 is directed to a control counter 75 to reset its count. The control counter 75 receives clock pulses from the clock 20 via NAND gate 74, and is configured to function as a well known binary ripple counter. An output is taken from output line $Q_5$ to a delay circuit 82, the output appearing in cycles after each of $2^5$ clock pulses, so long as the counter is counting. Additionally, outputs are taken at output lines $Q_9$ and $Q_{10}$, and directed to a NAND gate 76. The output from the NAND gate 76 is fed back to the NAND gate 74 to produce an enable signal to permit the clock pulses to pass. The output from the NAND gate 76 is also directed to the delay circuit 82.

In operation of the control counter 75, briefly, the control counter counts pulses from the clock 20 from an initial time until both $Q_9$ and $Q_{10}$ outputs are simultaneously "high" ($[2^9 + (2^9/2)]$ clock pulses). At that time, the output signal from the NAND gate 76 changes state, and the clock pulses are no longer able to be transmitted through the NAND gate 74, thereby stopping the count of the control counter 75. This time period is the "control interval" above defined. Upon the detection of an R-wave, a stimulation pulse, or an interference pulse by the R-wave detector and amplifier 54, the control counter is reset to begin its count anew. Simultaneously, the delay circuit 82 to which the outputs $Q_5$, $Q_9$ and $Q_{10}$ are applied (the concurring states of the $Q_9$ and $Q_{10}$ outputs being applied via a NAND gate 76), transmits a reset signal from its output through a NAND gate 50 to reset the asynchronous interval counter 25.

Thus, if an R-wave or interference pulse is received prior to the completion of the count by the asynchronous interval counter 25, the asynchronous interval counter 25 will be reset to begin timing the next heartbeat interpulse period, in the manner of a demand heart pacer. If no such resetting signal is forthcoming within the asynchronous interval, an output stimulation pulse is produced for delivery to the heart, as above described, Additionally, a mode switch 90 is provided to the delay circuit to render the natural hearbeat detection portion of the circuitry inoperable for test purposes.

The heart pacer circuit 10 of FIG. 1 is illustrated in greater detail in FIGS. 2 and 4, to which reference is now made.

DC electrical power is supplied to the circuit 10 by a power supply circuit 11. The power supply circuit 11 includes two batteries 12 and 13 and two diodes 14 and 15 connected respectively in series therewith. The series connected batteries and diodes are connected in parallel, as shown, to produce a negative voltage $-V$ at terminal 17 (hereinafter referred to as a "low" state) with respect to a ground potential at terminal 16 (hereinafter referred to as a "high" state). The power supply is connected to each of the various circuits of the pacer 10, the points of such connections being as shown.

The clock 20, in the illustrative embodiment, is of the astable multivibrator type, and includes circuit means for adjustably controlling its frequency. The frequency adjustment means includes a fixed resistor 22 in series with a variable resistor 23. A capacitor 21 connects the variable arm or wiper of the resistor 23 to the clock. The variable arm or wiper of the resistor 23 is additionally connected to the clock, whereby adjustment of the frequency can be precisely controlled. (The capacitor 21 may be connected, for example, between pins 1 and 3 and the resistor 22 to pin 2 of a digital integrated circuit such as CD 4047, as shown in FIG. 4). In the illustrative embodiment, the clock is designed to have an output upon line 24 of frequency of 2,688 Hertz as a uni-directional square wave train of pulses. Thus, the pulse period of the clock pulses is about 0.372 milliseconds.

The pulses from the clock 20 are delivered upon output line 24 to the asynchronous interval counter 25 to a clock input thereof. An output of the asynchronous interval counter 25 is taken from the output line $Q_{12}$ and directed to the pulse width regulator 28. The output at $Q_{12}$ will change from low to high is about 761.9 milliseconds, this being the approximate asynchronous interval (except for various delays below described).

The pulse width regulator 28 includes two J-K masterslave flip-flops 100 and 101. The J input of the flip-flop 100 is connected high, and the K input is connected low. The set terminals are connected low as is the reset terminal of the flip-flop 101. The Q output of the flip-flop 100 is connected to the J input of the flip-flop 101, and the $\overline{Q}$ output of the flip-flop 100 is connected to the K input of the flip-flop 101. The Q output of the flip-flop 101 is connected to the reset terminal of the flip-flop 100, and the output $\bar{Q}$ of the flip-flop 101 is the output from the pulse width regulator 28. The clock pulses upon line 24 are connected to the clock input of the flip-flop 101 and the output $Q_{12}$ of the asynchronous interval counter 25 is connected to the clock input of the flip-flop 100.

In operation of the pulse width regulator 28, when the output upon line $Q_{12}$ of the asynchronous interval counter 25 goes from low to high, the high state at the J input of the flip-flop 100 is moved through to the Q output thereof, thence to the J input of the flip-flop 101. Upon the occurrence of the next clock pulse upon line 24, the high state upon the J input of the flip-flop 101 is moved through to the Q output, thereby resetting the flip-flop 100 to its initial condition with its output Q being low. Concurrently, the output $\bar{Q}$ of the flip-flop 101 produces a change from its normally high to a low state, to produce a pulse for initiating a stimulation pulse from the amplifier 30 and to produce a resetting pulse upon the line 26 to reset the asynchronous interval counter 25. Upon the occurrence of the next clock pulse upon line 24, the low output then existent upon the output Q of the flip-flop 100 appearing at input J of the flip-flop 101 is moved through to the Q output of the flip-flop 101. Concurrently, the $\bar{Q}$ output of the flip-flop 100 returns to its normally high state, thus ending the output pulse from the pulse width regulator 28.

The output pulse from the pulse width regulator 28 is delivered to the amplifier 30, which includes two n-p-n transistors 32 and 36. The output signal from the pulse width regulator 28 is conducted through a resistor 31 to the base of the transistor 32. A resistor 33 connects the collector of the transistor 32 to ground 16, and the emitter is connected to a negative terminal 17. A capacitor 34 is connected between the collector of the transistor 32 and the emitter of the transistor 36. The emitter of the transistor 32 is connected by a resistor 37 to the base and by a resistor 35 to the emitter of the transistor 36. A second capacitor 39 is connected between the collector of the transistor 36 and the output heart terminals. A resistor 41 is connected between the collector of the transistor 36 and ground. A zener diode 40 is connected between the heart output line and ground 16 to protect the circuit against defibrillation pulses that may be encountered.

In operation of the amplifier 30, the amplifier circuit 30 functions as a voltage multiplying circuit. Between pulses, a voltage is built up upon the capacitors 34 and 39. Upon the application of a pulse to the base of the transistor 32, the transistor 32, and, consequently, the transistor 36, is biased into conduction. The transistor 36, becoming essentially saturated, connects the capacitors 34 and 39 in series, thereby producing a voltage of increased magnitude upon the line 53 for delivery to the output terminals 51.

The signals upon the line 53 (being the stimulation pulses produced by the amplifier 30 and the signals conducted to the circuit upon the terminals 51) are transmitted to the R-wave detector and amplifier 54. The signals are coupled into the amplifier by a resistor 55 and a capacitor 61, which filter some low frequency noise and block direct current noise. A diode 56 clips the voltage of a pacer produced pulse so that on being fed back to the R-wave detector, the amplifier is not overloaded. The adjustable arm 59 of a variable resistor 58 is connected to the capacitor 61 and to an input of a linear high gain amplifier 64. The variable resistor 58 and the resistors 57 and 60 constitute a voltage divider between ground 16 and the negative terminal 17 to establish the threshold voltage on the amplifier 64. A capacitor 62 and a resistor 63 are connected in series between the ground terminal 16 and the other input to the amplifier 64 to provide a filter for excluding undesirably low frequencies. A resistor 66 bridges the two contacts identified as 7 and 5 in amplifier 64 (which can be, for example, an integrated circuit type CA3078). A capacitor 45 bridges two contacts identified as 1 and 8 in the amplifier 64. A resistor 65 interconnects the output 46 of the amplifier 64 and the input of the amplifier 64.

An analog to digital converter 67 is an integrated circuit, such as type CD4007, comprising several components. A field-effect transistor 68 serves as a threshold detector. The output 46 of the amplifier 64 is connected to the gate of the threshold detector 68. The source of threshold detector 68 is connected to ground 16, and the drain is connected through the resistor 69 to the negative terminal 17. The signal developed across the resistor 69 is amplified in amplifiers 70 and 71 to provide a signal indicating the receipt of an R-wave or an interference pulse by the amplifier 54.

The output from the amplifier 71 is conducted on a line 72 to a reset input of the control counter 75. As indicated above, the pulses from the clock 20 are conducted upon line 24 through an input of the NAND gate 74 to the clock input of the control counter 75. Outputs are taken upon logic output terminals $Q_5$, $Q_9$ and $Q_{10}$. The outputs on terminals $Q_9$ and $Q_{10}$ are connected to the inputs of the NAND gate 76, the output of which is fed back on line 81 to another input of the NAND gate 74 to control the passage of the clock pulses therethrough to the clock input of the control counter 75. The line 81 is also connected to the delay circuit 82, and the output $Q_5$ is also conducted to the delay circuit all as described below. It can be seen that the line 81 is normally high, (because of the truth-table output of the NAND gate 76), unless both $Q_9$ and $Q_{10}$ outputs are both high. In this event, the line 81 is low, thereby presenting a non-varying high input to the clock input of the control counter 75 via the NAND gate 74. Thus, in this condition, the control counter will cease to continue its count until it is reset by an R-wave indicative signal.

The delay circuit 82 includes two J-K master-slave flip-flops 102 and 103. The output from the NAND gate 76 is connected to the clock input of the first flip-flop 102. The output 80 from the $Q_5$ terminal of the control counter 75 is connected to the clock input of the second flip-flop 103. The J input of the flip-flop 102 is connected high, and the K input is connected low. The set terminals of both flip-flops are connected low. The Q and $\bar{Q}$ outputs of the flip-flop 102 are connected to the J and K inputs, respectively, of flip-flop 103. The Q output of the flip-flop 103 is connected to the reset terminal of the flip-flop 102, and the $\bar{Q}$ output of the flip-flop 103 produces the output of the delay circuit 82 for delivery to reset the asynchronous interval counter 25. The reset terminal of the flip-flop 103 is connected to ground 16 (high state) through a normally-open mode switch 90. The reset terminal of the flip-flop 103 is normally maintained at a negative potential (low state) by connection to a negative voltage terminal 17 through a resistor 91.

The output $\bar{Q}$ of the flip-flop 103 is conducted on line 83 to one input of the NAND gate 50 (the other input being the output from the pulse width regulator 28 upon line 29 as above described). The mode switch 90 is connected to the reset terminal of the flip-flop 103 to selectively apply a high state from the ground terminal 16 or a low state from a negative terminal 17 via resistor 91. The closing of the mode switch from its normally-open position applies a continuous resetting high state to disable the flip-flop 103, thus preventing the application of resetting pulses from the control counter 75 to the asynchronous interval counter 25, constraining the pacer 10 to an asynchronous mode. The mode switch 90 can be a magnetically activated reed switch, such switches being well known in the art.

Figure 3:
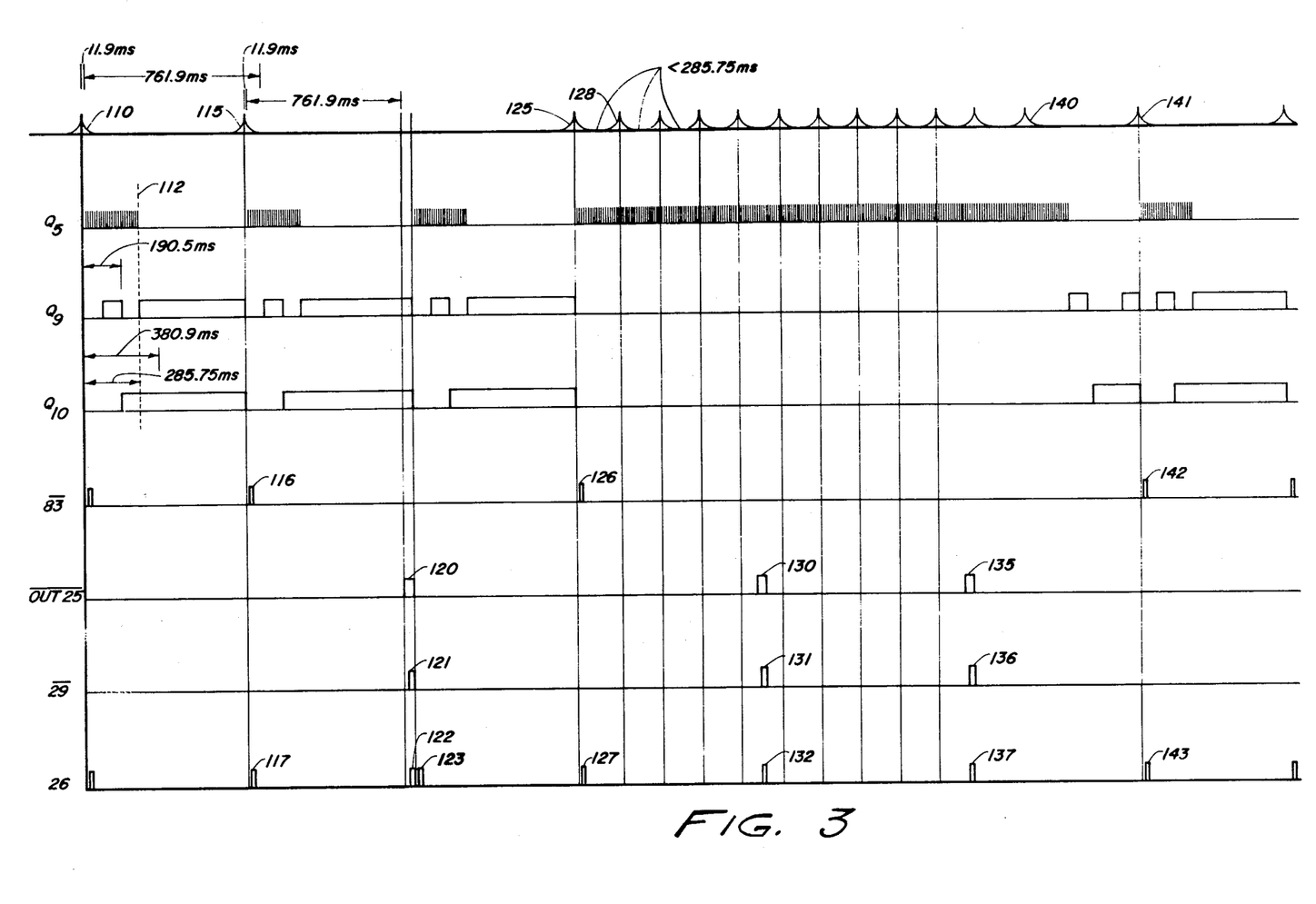
FIG. 3 is a series of vertically aligned graphs showing the various pulses and states produced at selected points in the circuit illustrated in FIG. 2.

The operation of the heart pacer circuit 10 is explained in conjunction with the various graphs set forth in FIG. 3.

In FIG. 3, the voltages at the various points in the circuit are shown along the left side of the graph (some being inverted for clarity, as indicated by a bar (—) over the number), represented as a function of time. (It should be also noted that the pulses illustrated are intended to show their relative occurrences, and that the sizes, shapes, and proportions thereof have been exaggerated or distorted for clarity of illustration and ease of description.)

Assuming that the heart has been pulsing normally at intervals less than the asynchronous interval measured by the pacer circuit 10, the operation is initially as follows. A first pulse 110 is detected and amplified by the R-wave detector and amplifier 54, which resets the control counter 75 enabling it to begin its count. This is achieved, as above indicated, upon being reset by the concurrence of low outputs on terminals $Q_9$ and $Q_{10}$, producing a high state on line 81. This high state on line 81 enables the clock pulses on line 24 to pass through the NAND gate 74 to the clock input of the control counter 75. The output of terminal $Q_5$ then cycles each $2^5$ clock pulses, of about 11.9 milliseconds, as shown on the graph $Q_5$. This repeated output continues until the concurrence of a high output upon terminals $Q_9$ and $Q_{10}$, as shown by the dotted line 112, as can be seen from the graphs of the outputs $Q_9$ and $Q_{10}$. This concurrence occurs at a time approximately 285.75 milliseconds from the occurrence of the heart pulse 110. (It should be appreciated that the asynchronous interval counter was additionally reset a delayed time after the control counter was reset, and it is concurrently counting clock pulses toward its $Q_{12}$ output. The mechanics of this resetting is below discussed.)

The next naturally produced heart pulse 115 is detected by the R-wave detector and amplifier 54 prior to the reaching of the $Q_{12}$ count by the asynchronous interval counter (at approximately 761.9 milliseconds plus the 11.9 millisecond delay, as shown in the scale above the graph). At this instant, the control counter 75 is reset to begin its count anew. At the same time, however, the state upon line 81 is changed from low to high. This change activates the flip-flop 102, moving the high state of the j input to the Q output and the J input of the flip-flop 103. When the output upon line 80 from the terminal $Q_5$ of the control counter 75 changes to a high state, approximately 11.9 milliseconds later, the high state on the J input of the flip-flop 103 is transferred to the Q output thereof, to reset the flip-flop 102. At the same time, the $\overline{Q}$ output of the flip-flop 103 changes from its normally high state to a low state upon line 83, shown as pulse 116 on an inverted graph $\overline{83}$. This pulse 116, when applied through the NAND gate 50, produces a resetting pulse 117 upon line 26 to the asynchronous interval counter 25. It should be noted that the resetting pulse occurs approximately 11.9 milliseconds after the occurrence of the heart pulse 115. Thus, the count of the asynchronous interval counter 25 begins at a delayed time period after the reception of the heart pulse 115.

Next, assuming that no natural heart pulse is produced within the interval after the previous heart pulse 115 prior to the reaching of the state change produced by the clock pulse count upon terminal $Q_{12}$ of the asynchronous interval counter 25 ($[2^{12} \div 2]$ clock pulses), the terminal $Q_{12}$ of the asynchronous interval counter 25 will change states, as shown by the pulse 120 on the line out $\overline{25}$. This change is state, as above indicated, will produce an output pulse 121 upon line 29 from the pulse width regulator 28, as shown on the line $\overline{29}$. The pulse 121, produces a resetting pulse 122 upon the line 26, thereby resetting the count of the asynchronous interval counter 25. Additionally, the pulse 121 on the line 29, after being amplified and delivered to the heart as a stimulation pulse, is conducted through the R-wave detector and amplifier 54 to reset the control counter 75. Thus, after the termination of the stimulation producing pulse 122, the control counter again begins its count, producing a number of pulses as can be seen on the lines $Q_5$, $Q_9$ and $Q_{10}$.

When the control counter 75 which has then begun to again count reaches the count to produce the first output change of state on $Q_5$, another resetting pulse 123 is produced on the line 26. This pulse is generated in the same fashion as the resetting pulse 117, above explained, and again resets the asynchronous interval counter 25. It can therefore be seen that the demand interval is equal to the sum of time for the asynchronous interval counter output on $Q_{12}$ to change states plus the time for the control counter output on $Q_5$ to change states, about 761.9 + 11.5 milliseconds plus whatever delays are introduced by the circuit elements themselves (such as the delays in the amplifiers 54 and 30).

Assuming next that a number of interference pulses are then detected having an interpulse period less than 285.75 milliseconds (the time at which the output $Q_9$ and $Q_{10}$ terminates the counting of the control counter 75), the following operation will occur. Since the $Q_9$, $Q_{10}$ high concurrence count was reached in the previous demand cycle, the first pulse 125 in the train of pulses will change the state of line 81 from low to high, to thereafter generate a resetting pulse 126 on the line 83 from the delay circuit 82 and a resetting pulse 127 on the line 26. The count of the asynchronous interval counter 25 is thus reinitiated from this time. Prior to the control counter 75 reaching the count corresponding to the concurrence of high outputs on $Q_9$ and $Q_{10}$ another interference pulse 128 is received. This resets the control counter 75, but since no high concurrence occurred on the output terminals $Q_9$ and $Q_{10}$, no change in state is produced on the output line 81. Thus, when the subsequent $Q_5$ change in state is reached, no resetting pulse is developed by the delay circuit 82 on the line 83. The asynchronous interval counter 25 is, therefore, allowed to continue counting without being reset, so long as the interference pulses continue. Thus, at the reaching of the change in state upon the output terminal $Q_{12}$, an output pulse 130 will be developed at the output $Q_{12}$ shown on line $\overline{OUT\ 25}$. This output, as before, will produce a stimulation pulse 131 upon the line 29 for amplification and delivery to the output electrodes 51.

The stimulation pulse 131 will produce a resetting pulse 132 on the line 26 to reset the asynchronous interval counter 25. Assuming the interference pulses continue the asynchronous operation will continue, developing an output pulse 135 on the $Q_{12}$ terminal on the reaching of the next asynchronous interval count. This, as before, will produce pulses 136 and 137 on lines $\overline{29}$ and 26, respectively. It should be noted that in this "interference mode" of operation, the output pulse interval is only the interval determined by the asynchronous interval counter (about 761.9 milliseconds), since no delay is produced by the control counter 75 and the delay circuit 82. The heart pacer circuit 10, therefore, has a different rates in the demand mode and in the interference mode due to the injection of the delay by the control counter 75 and the delay circuit 82.

It can be additionally seen that the control counter 75 defines a refractory period during which the reception of an interference pulse will not provide a resetting pulse to the asynchronous interval counter 25, that period being the time for the control counter to count to the concurrence of high outputs on terminals $Q_9$ and $Q_{10}$. It should be noted furthermore that the refractory period is extendable if such R-wave pulse is received during the count prior to the reaching of the high concurrence of terminals $Q_9$ and $Q_{10}$, since the control counter 75 is reset upon its each occurrence. Thus, the refractory period can be indefinitely reset should the appropriate resetting pulses be applied to the control counter 75.

Once the count has reached the concurrence of high outputs on $Q_9$ and $Q_{10}$, hoever, the pacer is in an "alert" state, since the reception of an R-wave or interference pulse will produce a change in state upon line 81 to produce a resetting pulse to the asynchronous interval counter 25. This alert state is illustrated in the portion FIG. 3 immediately following the heart pulse 140. After the control counter 75 has reached the concurring high states on output terminals $Q_9$ and $Q_{10}$, even if only briefly, as illustrated, the reception of a pulse 141 will produce a change in state on line 83, as shown by pulse 142 on line $\overline{83}$. The pulse 142, of course, will produce a resetting pulse 143 upon line 26 to the asynchronous interval counter 25.

The schematic representation of FIGS. 1, 2 and 4 features the use of integrated circuit components which can be purchased and used as such. Components can be selected in the preferred embodiment as follows:

| Resistors | |
|---|---|
| 22 | 2,000Ω |
| 23 | 2 MΩ |
| 31,38,55 | 10,000Ω |
| 33,35 | 4,700Ω |
| 37 | 62,000Ω |
| 57,60,91 | 1 MΩ |
| 65 | 4.7 MΩ |
| 66 | 10 MΩ |
| 58 | Variable 0-2 MΩ |
| Capacitors | |
| 21 | 100 pf |
| 34,39 | 39 μf |
| 45 | 50 pf |
| 61 | 100 nf |
| 62 | 220 nf |
| Batteries | |
| 12,13 | Li-2 thionyl chloride cells |
| Diodes | |
| 40 | zener |
| 56 | within IC type CA3093 |
| Integrated Circuits and Gates | |
| 20 | (clock) CD4047 |

-continued

| | |
|---|---|
| 25 | (rate counter) CD4040 |
| 28 | (pulse width regulator) CD4027 |
| 64 | (amplifier) CA3078 |
| 67 | (A/D converter) CD4007 |
| 70,71 | (inverter gates) part of A/D converter 67 |
| 75 | (control counter) CD4040 |
| 82 | (delay circuit) CD4027 |
| 50,74,76 | (NAND gates-parts A,B,C) CD4011 |

Although the invention has been described and illustrated with a certain degree of particularly, it is understood that the present disclosure has been made only by way of example and that numerous changes in the details of construction and the combination and arragement of parts may be resorted to without departing from the spirit and the scope of the invention as hereinafter claimed.

We claim:

1. A heart pacer for supplying stimulation pulses to electrodes adapted to be connected to a heart, comprising;
a source of clock pulses a plurality of which being spaced within an interval between normal heartbeats;
counting means for counting said clock pulses for producing an output upon reaching a pulse count corresponding to a predetermined interval within said interval between normal heartbeats, said counting means being reset upon reaching said count;
a stimulation pulse generator actuated by said counting means output to provide a stimulation pulse for delivery to said electrodes;
a detecting circuit for receiving signals from said electrodes for detecting and amplifying heartbeat indicative signals;
and control interval counting means for counting a preselected number of said clock pulses corresponding to a preselected refractory interval, said control interval counting means being reset by said heartbeat indicative signals, each control interval consisting of the sum of said refractory interval and a variable interval resulting from said control interval counting means being reset by said heartbeat indicative signals, if any, detected prior to the reaching of the count corresponding to said refractory period, said control interval counting means thereafter generating an output when actuated by heartbeat indicative signals to disable and reset said counting means.

2. A heart pacer according to claim 1 in which the pacer includes means for producing an interference mode when a particular control interval is extended by a plurality of heart indicative signals to at least equal said predetermined interval.

3. A heart pacer according to claim 1 further comprising means for resetting the interval counter including delay circuitry for disabling the interval counter for the duration of the delay interval, said delay interval being a small fraction of an interval within the range of intervals between normal heartbeats.

4. A pacer adapted to be connected to a d-c source and to a patient's heart to provide a heart stimulation pulse thereto in the absence of a normal heartbeat, comprising;
means for generating clock pulses;
a resettable interval counter for counting a predetermined number of clock pulses during a normal heartbeat interval and to thereafter generate an output signal;

an amplifier for converting said output signal into a heart stimulation pulse for delivery to the heart;

detection circuit means connected to receive heart signals, actuated by any of (a) heartbeat simulating interference signals, (b) heartbeat signals, and (c) stimulation signals, to generate an output state;

a resettable control counter for counting a selected number of clock pulses corresponding to a refractory period;

said control counter generating an output signal only upon being reset by said detection circuit output state after said refractory period is uninterruptedly counted;

and a delay circuit to which said control counter output is applied for providing a delayed output applied to reset said interval counter, whereby the interval preceding each stimulation pulse is the sum of at least said delay and said interval established by said interval counter, except when said control counter is reset by interference signals prior to said refractory period count.

5. The pacer according to claim 4 further comprising mode switching means for disabling said delay counter output pulse from resetting said interval counter.

6. The pacer in accordance with claim 4, comprising:
stimulation pulse width regulating means responsive to a controlled number of clock pulses actuated by said interval counter output signal to generate a widened pulse signal for application to said amplifier.

* * * * *